United States Patent [19]

Yan et al.

[11] Patent Number: 4,960,425
[45] Date of Patent: Oct. 2, 1990

[54] TEXTURED SURFACE FROSTHESIS IMPLANTS

[75] Inventors: John Y. J. Yan; Bobby K. Purkait, both of Santa Barbara, Calif.

[73] Assignee: Mentor Corporation, Goleta, Calif.

[21] Appl. No.: 393,113

[22] Filed: Aug. 4, 1989

Related U.S. Application Data

[63] Continuation of Ser. No. 54,607, May 27, 1987, abandoned.

[51] Int. Cl.$^5$ ............................ A61F 2/12; A61F 2/02
[52] U.S. Cl. ............................................. 623/8; 623/11
[58] Field of Search ........................ 623/7, 8, 1, 2, 10, 623/11, 12, 16, 18, 66; 128/DIG. 21; 606/228, 229, 215, 151, 152, 153; 604/890, 891

[56] References Cited

U.S. PATENT DOCUMENTS

| | | | |
|---|---|---|---|
| 3,600,718 | 8/1971 | Boone | 623/8 |
| 3,700,380 | 10/1972 | Kitrilakis | 623/1 |
| 4,531,244 | 7/1985 | Hamas | 623/8 |
| 4,596,577 | 6/1986 | Sato | 623/1 |
| 4,648,880 | 3/1987 | Brauman | 623/8 |
| 4,820,303 | 4/1989 | Brauman | 623/8 |

OTHER PUBLICATIONS

Picha et al., "Ion Beam Microtexturing of Biomaterials", MD & DI; Apr. 1984, pp. 39–42.

*Primary Examiner*—David J. Isabella
*Attorney, Agent, or Firm*—Blakely, Sokoloff, Taylor & Zafman

[57] ABSTRACT

A surgical prosthesis is disclosed having a textured exterior surface formed of non-absorbent material substantially free of pores and interstices. The invented device is usable for mammary and other implants. Various methods of manufacturing the device are also disclosed.

24 Claims, 2 Drawing Sheets

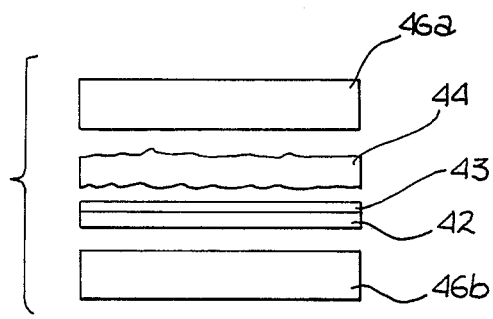
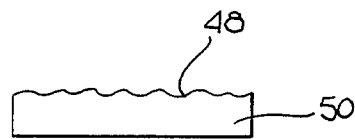
Fig. 4    Fig. 5
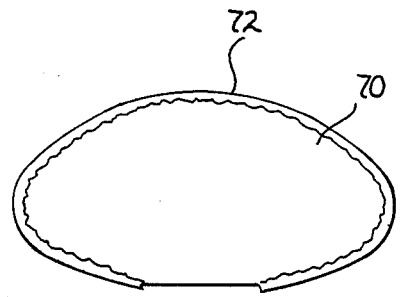
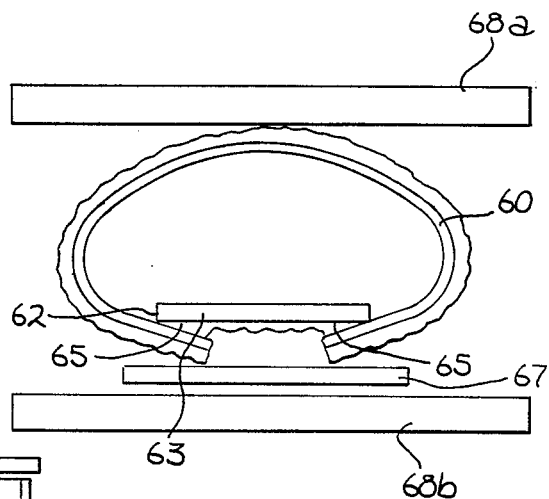
Fig. 6    Fig. 7
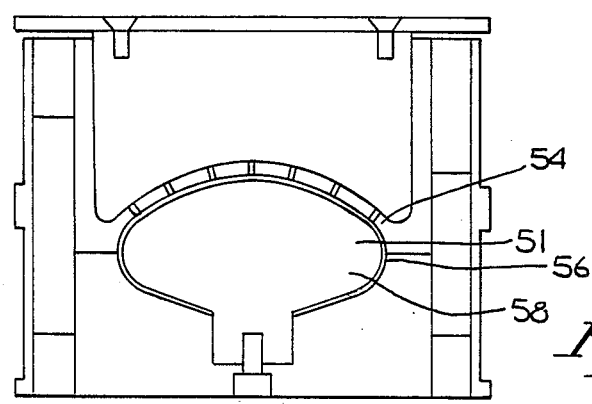
Fig. 8

TEXTURED SURFACE FROSTHESIS IMPLANTS

This is a continuation of application Ser. No. 054,607 filed 5/27/87 now abandoned.

FIELD OF THE INVENTION

This invention relates generally to prosthesis, and particularly, to an improved prosthesis for surgical implantation, such as a breast implant, having a textured non-porous exterior surface thereon.

BACKGROUND OF THE INVENTION

It is well-known in the field of plastic surgery to enlarge the female breast or replace other body organs or structures with prostheses which are surgically implanted therein. With respect to female breasts, in many instances it becomes necessary to remove the entire mammary gland or a substantial portion thereof as a result of cancerous infection or other disease. The surgical removal of the diseased body tissue leaves voids which may be filled by such a prosthetic implant. Such implants provide physical support for the surrounding body tissue and organs and in the case of voids near the skin, preserve the outward appearance of the body. When cancerous, pre-cancerous, or damaged tissue is removed, it is often possible to insert the prosthesis to be implanted through the same surgical incision used for removing the tissue. Particularly in the cases where a radical removal of tissue has occurred it is desirable to use an implant for the purpose of restoring the human body to its original normal form. The restoration of the normal appearance of the body has an extremely beneficial phychological effect on post-operative patients, eliminating much of the shock and depression that often follows extensive surgical procedures.

Among the various problems involved in prosthetic implants are those of preserving the natural shape of the body over time after implantation. Some prior art implants comprise an outer layer of sponge material which retains a relatively natural softness and resiliency similar to the replaced body tissue. However, the inherent porosity of such sponge material has also been a source of considerable inconvenience and disappointment because the sponge eventually becomes invaded with connective tissue, sometimes called capsule formation, throughout all or a major portion of the implant. The connective tissue, being fibrous, shrinks as it ages, sometimes called capsular contraction, resulting in the compression of the implant thereby causing the implant to lose both its original size and shape and its original resiliency. Cases are known where shrinkage has been as much as 20 to 30% of the original size. These changes in shape, size and resiliency may be distressing and embarrassing to the patient and are obviously undesirable.

Other prior art prosthesis comprise a smooth outer surface so that there can be no infiltration of the fibroblasts into the surface of the prosthesis. However, it is difficult to obtain anchoring of the prosthesis to the body because of the difficulty of the connective tissue grown thereon to form a satisfactory attachment thereto. Also, these smooth surface prostheses which are covered with a cellular layer which can not become infiltrated by living tissue, but instead, have a more or less external surface which is formed of an impervious material, so that body fluid can and often does accumulate between the prosthesis and the living tissue. This fluid accumulation may be directly or indirectly related to infection in the patient at the site of the fluid accumulation. Also, in severe cases, the infection may cause necrosis of the tissue in the location of the prosthesis.

Another type of breast prosthesis which is known in the art has a smooth surface to which is glued a porous polyurethane foam or Dacron velour material. It has been suggested that these porous surfaces allow the penetration of tissue and fluids from the surrounding tissue. It has also been suggested that such polyurethane coated prosthesis inhibit the problems of capsular contraction. (See U.S. Pat. No. 4,648,880 and Pennisi, Aesth. Plast. Surg. 9:73-77, 1985). These porous surface prostheses are thick and not very compliant, and therefore, in some cases, are difficult to insert beneath the skin with a small surgical incison. As a result, large incisions which cause unsightly scars may be necessary in order to provide a sufficiently large hole for proper insertion. These porous prostheses are also absorbant to bacterial containing body fluids and thus make infection control difficult. In addition, if the porous material is polyurethane foam, there have been a number of reports that the foam disintegrates in the body after a few months causing sever rashes. Also marked foreign body reaction may also be observed with these foam implants. (Plastic and Reconst. Surg. 61, No. 1, 1978.) Rashes have also been known to occur soon after implantation in some instances, possibly as a result of a body reaction to the antibotic solution in which the polyurethane coated prosthesis is dipped prior to implantation.

In the standard process for manufacturing surgical prosthesis, and particularly, mammary implants, a shell of desired thickness is formed having the desired shape for the particular implant and purpose. These shells may be single lumen, multilumen or expandable type prosthesis such as those used for tissue expansion. The shell generally has a circular hole, termed a patch hole. The patch hole is then covered with a patch which is attached thereto using silicone rubber o other similar biocompatible adhesive. The prosthesis is then filled through a small fill hole with saline, gel, foam, combinations of these materials or other suitable material known in the art and the fill hole is sealed. The prosthesis, having a smooth exterior, is then sterilized and implanted, or it may be covered with a foam material as described above prior to sterilization and implantation.

The above-described problems are overcome by the present invention which is described briefly below.

SUMMARY OF THE INVENTION

The present invention comprises a surgical prosthesis for use in augmentation mammaplasty and reconstructive surgery, having an exterior surface that is partially or fully textured. The textured surface consists of a plurality of substantially microscopic peaks and valleys substantially free of pores or interstices. The textured surface permits the infiltration of tissue and fluids to enhance anchoring of the prosthesis in the body; however, the lack of pores and interstices prevent pooling or sequestration of body fluids which may otherwise increase the risk of infection. The textured surface is made of silicone rubber or other similar plastic material which is non-absorbent to body fluids, thereby inhibiting otherwise uncontrollable infection.

The textured surface may directly or indirectly disrupt capsule formation around the prosthesis, permit anchorage of tissue to the prosthesis to prevent movement at the tissue prosthetic interface and eliminate space at the interface which can lead to bacterial infection and possibly tissue necrosis. These factors may further directly or indirectly lower or eliminate capsular contracture incidence which has been observed with prior art surgical prosthesis.

The surgical prosthesis may be used as mammary implants or other body implants such as penile prosthesis, and maxillofacial prosthesis, and for a tissue expander. The shell of the prosthesis may be single or multilumen or an expandable type and may be of any size and shape.

Additionally, various processes for manufacturing the invented textured prosthesis are also disclosed. In one such process a formed shell having a smooth exterior surface is disposed on a flattened or slightly curved disk and is coated on its exterior surface on one or both sides of the disk with unvulcanized or partially vulcanized silicone. The silicone layer is then covered with a porous or textured medium and the entire combination is compressed between platens for a short time until a textured surface is formed in the silicone layer. The texturized shell is then cured. After curing, the patch hole is covered with a patch which may or may not be texturized utilizing a similar procedure.

In another embodiment, the shell is tightly wrapped around a mandrel having a corresponding shape. The shell is then coated with an unvulcanized or partially vulcanized silicone coating which is thereafter coated with a porous or textured medium having a similar shape. A form fitting press may then be applied thereto or direct pressure from the porous medium may be applied to form a textured surface on the silicone coating. The prosthesis may then be cured on or off the mandrel and patched as aforesaid.

In another embodiment a mandrel in the shape of the prosthesis and having a texturized surface is coated with silicone rubber or other plastic biocompatible material. A shell is then disposed on the mandrel and the coating is cured on the shell. The texturized shell is removed from the mandrel, turned inside out and patched and filled as discussed above.

In yet another embodiment, a prosthesis having a sufficiently thick shell is etched using ion beam, chemical or other physical techniques, such as scratching, carving, burning, or the like, to cause a sufficient texturization in the outer surface thereof.

In yet another embodiment of the present invention the prosthesis is directly molded on a mold having a textured surface on at least one side. If the textured surface is on the inside of the prosthesis shell, the shell can be turned inside out, prior to assembly.

It is an object of the present invention to provide a surgical prosthesis having a textured surface formed of silicone or the like which is non-porous or substantially non-porous.

It is another object of the present invention to provide a prosthesis for surgical implantation which is capable of relatively efficient fixation to the body.

It is yet another object of the present invention to provide a surgical prosthesis in which the entire prosthesis is transfer, compression or injection molded. In injection molding, the mold can have a textured surface which forms a texturized prosthesis directly therein.

Other processes are disclosed in detail below.

BRIEF DESCRIPTION OF THE DRAWINGS

FIG. 4 illustrates a process for manufacturing a patch for the invented prosthesis.

FIG. 5 illustrates a texturized patch for the invented prosthesis.

FIG. 6 illustrates yet another embodiment for manufacturing the invented prosthesis utilizing a textured mandrel.

FIG. 7 illustrates a sectional view of the patching of a shell of a textured prosthesis.

FIG. 8 illustrates an injection mold for molding a texturized prosthesis.

FIG. 9 is a 64× magnification of microscopic view of a texturized prosthesis surface (top view).

FIG. 10 is a 50× magnification of a microscopic view of a texturized prosthesis (cross-sectional view).

FIG. 11 is a 50× magnification of a microscopic view of a 200 micron pore size reticulated foam which may be used as a textured medium to texture the surface of the prosthesis.

DETAILED DESCRIPTION

The present invention is directed to a surgical prosthesis for implantation in a body for mammary, urological, gastrointestinal, or other organo-systems in which either a portion of the body has been removed or augmentation thereof is required or desired.

The present invention is particularly directed and useful as mammary implants which comprise a large portion of the surgical implantation which is presently performed. However, the presently described processes and prostheses are suitable for other surgical implants a well. It will be understood by a person of ordinary skill in the art that in describing the invented process with reference to mammary implants, the inventors intend to include within the scope of their invention all surgical implants of the type wherein a textured surface may be useful.

Figure 1:
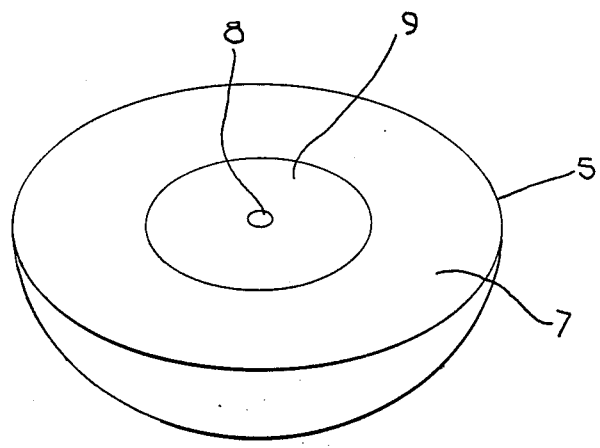
FIG. 1 illustrates a perspective view of a texturized mammary prosthesis.

FIG. 1 shows a mammary implant 5 having a completely texturized outer surface 7, a patch 9 and a fill hole 8. Of course, other shapes for the implants can be used and are contemplated as being within the scope of the present invention, such as for implantation for partial mastectomies and for augmentation surgery. It will also be appreciated that while the description herein generally relates to prosthesis having a textured surface around its entire outer surface, a partial covering of the outer surface with a textured coating or topography is also contemplated.

As mentioned above, the textured, non-porous coating on the exterior surface permits greater and faster adhesion of the implant to the body by providing stronger attachment sites of the fibroblast connective tissue formed by the body in response to the implant. In addition dead space is eliminated or minimized relative to smooth surface prosthesis, thereby minimizing friction irritation. Capsular formation and the potential resulting undesirable effects of capsular contraction may also be reduced.

As used herein, the term "textured" or "texturized" used in conjunction with the present invention means a surface having minute indentations, deformations and/or raised portions on the subject surface. The width of each individual raised portion or indentation generally ranges in size from 0.0003 to 0.10 inches. The depth of the indentations and raised portions is on the order of 0.0003 to 0.030 inches. Thus, the general appearance of the prosthesis is that of an opaque surface, slightly rough to the touch.

An important feature of the textured surface on the subject invention is the lack or substantial lack of pores or interstices which can accumulate or sequester body fluids and provide a volume in which infection can proliferate. The textured surface has raised portions or indentations which are generally transverse to the plane defined by the surface. The projections on the surface of the textured prosthesis may be generally columnar if a screen with round perforations therein is used as the textured medium. The projections may be irregularly shaped if foam material is used as a texturized medium. The projections or indentations may be regular geometric shapes if a screen with a crossed or knitted pattern is used to texturize the surface. The essential difference between the present invention and prior art textured prosthesis utilizing woven, knitted, braided or felt fiber coatings on the exterior thereof, such as Dacron velour, is that the present invention generally lacks pores or interstices disposed in a direction primarily parallel to the surface of the prosthesis. Fiber materials, on the other hand, tend to have such pores or interstices parallel to the surface which can provide pockets capable of sequesting the body fluid.

As used herein, the term "absorbent" means a material itself, or a material having a particular structure making it capable of retaining a liquid by any of a number of different mechanisms. For example, some materials such as paper and cotton, absorb liquid into the individual fibers comprising such materials. Other materials may be comprised of fibers which are not of themselves absorbent, but which absorb fluid by capillary action diffusion or similar physical properties as a result of their structure. For example, the polyurethane fiber forming a foam coating disclosed by Pangman U.S. Pat. Nos. 3,366,975 and 3,683,424, are described as having non-absorbent fibers. However, the foam materials of Pangman are very absorbent as a result of liquid being drawn into the pores and interstices of the foam by diffusion or capillary action. The present invention comprises a substantially non-absorbent coating, as the word "absorbent" is used herein.

Figure 2:
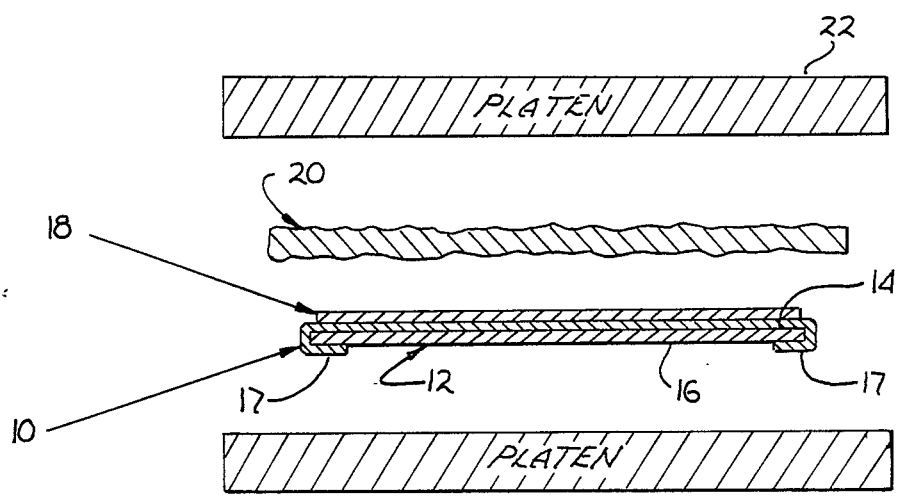
FIG. 2 illustrates an exploded view of one process for manufacturing the texturized prosthesis utilizing a flat disk.

FIG. 2 illustrates an exploded view of a portion of one method of manufacturing the invented prosthesis. As shown in FIG. 2, an unpatched surgical prosthesis 10, such as for use as a mammary implant, is stretched over a flat or low curvature disk 12 having a circular, oval or other suitable shaped cross-section. The majority of the exterior surface of the prosthesis is located on the upper side 14 of the disk 12. A layer or multiple layers of unvulcanized or partially vulcanized silicone 18 with a total thickness of 0.003 inches to 0.10 inches covers the upper surface 14 of the prosthesis. Only a small portion 17 of the prosthesis 10 is disposed on a lower surface 16 of the disk 12. In this configuration the silicone covering is disposed across almost the entire exterior surface of the prosthesis such that no seam will appear visible at the top or substantially any of the sides of the finished prosthesis.

In the next step of the first process disclosed herein, the silicone covering 18 is covered with a porous o textured medium 20. This porous or textured medium 20 may be, for example, foam, a perforated screen or a specially molded form having a textured surface of the particular desired design and topography. In the presently preferred embodiment the medium comprises reticulated foam having approximately 100 pores per inch (100 ppi). The entire assembly including the disk 12, prosthesis 10, silicone layer 18 and porous or textured medium 20 is then compressed using either cold or hot compresive platens 22a and 22b. The use of hot platens in the compression of silicone and similar materials is well known in the art. If cold platens are used, the silicone must be carefully handled until it is vulcanized, or partially vulcanized. In the presently preferred embodiment, cold platens are used having a compressive fore of 80 pounds per square inch for 0.5 to 2.5 minutes.

After compression, the platens 22a and 22b are removed and the medium 20 is also removed leaving a texturized imprint in the silicone layer 18. The prosthesis 10 with the imprinted texturized silicone layer 18 is then removed from the disk 12 and the prosthesis with the imprinted silicone layer is cured at vulcanizing temperatures, as is known in the art. In particular, in the preferred embodiment, curing takes place at approximately 350° to 400° F over a period of four hours, although the particular temperature and time may vary depending upon the particular materials used. In the preferred embodiment, the silicone material is obtained from Dow Corning.

In the preferred embodiment, shown in FIG. 7, the patch is a textured and adhered to the shell in a single step. As shown, a textured shell 60 is provided, as described above. An untextured patch 62 comprising a vulcanized layer of silicone sheeting 63 and an unvulcanized layer of silicone 61 is also provided and disposed within the shell 60 with the unvulcanized layer 61 facing outward and the perimeter 65 of the patch 62 overlapping with the edge 66 of the shell 60. A textured or porous medium 67 is disposed over the patch 62 and the entire assembly is compressed between hot platens 68a and 68b at 350° F and 80 psi for 2.5 minutes. The platens 68a and 68b and the medium 67 is removed, and the patched shell is cured in an oven at 350° F for 4 hours.

In an alternative method, the patch is preferrably texturized as shown in FIGS. 4 and 5 in a manner similar to the process for texturing the prosthesis shell as described above. FIG. 4 is an exploded view of the process for making a textured patch. A sheet of partially vulcanized silicone sheeting 42 is formed from unvulcanized silicone, commercially available from Dow Corning calendered into sheets, vulcanized and then coated with unvulcanized silicone 43. The sheeting is covered with a porous or textured surface medium 44 of the same type as described above. The combination of sheeting 42 and medium 44 are compressed between platens 46a and 46b to form a patch 50 having a single sided texturized surface 48 as shown in FIG. 5. The textured patch is preferably placed on the inside of the prosthesis with unvulcanized or partially vulcanized silicone facing outward and a washer or ring of unvulcanized silicone disposed therebetween to adhere the patch to the shell. The surface facing inward toward the inside of the prosthesis is precured so that it does not stick to the inner surface of the prosthesis shell.

Whichever process is used for texturing the patch hole, the prosthesis with the textured uncured patch hole is then cured in the same manner as discussed above, or as otherwise required by the manufacturer's instructions.

The above-described process provides a prosthesis having no seam on its exterior surface, with its entire surface being texturized. The following procedure ma be used in the manufacture of a surgical prosthesis having a textured surface except that a seam or overlapping of the silicone layers on the exterior surface will be provided. In this embodiment, the prosthesis is stretched over a disk such that the outer diameter is at or near the edge of the disk. One silicone layer with a thickness of between 0.003 and 0.10 inches are placed on the top and bottom sides of the disk and a porous or textured medium is placed over each silicone layer. It is not at all necessary to texturize the two sides of the surgical prosthesis at the same time or in any particular sequence. The entire prosthesis is patched in this manner as well. The entire prosthesis is then cured in accordance with the above-described process and may then be filled as discussed below by any other procedure known in the art. In this manner, in a single step, a partially textured surgical prosthesis is provided.

Figure 3:
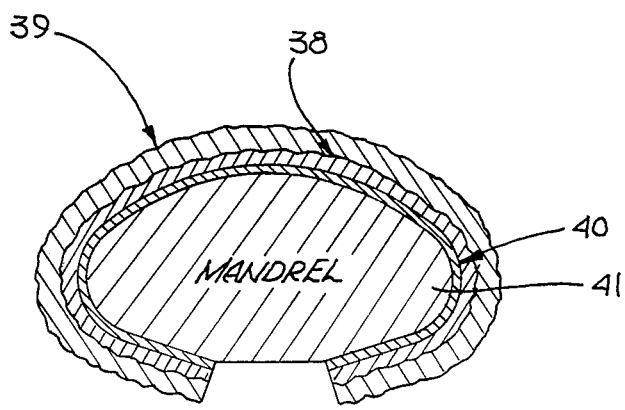
FIG. 3 illustrates another embodiment of the process for manufacturing the invented prosthesis utilizing a mandrel.

In yet another embodiment of the present invention as shown in FIG. 3 a surgical prosthesis 40 is disposed on a mandrel 41 having a smooth exterior surface. The prosthesis 40 is then coated with unvulcanized or partially vulcanized silicone 38 coated over the surgical prosthesis 40. A porous or textured medium 39 is then fitted over the silicone layer 38 with sufficient pressure to provide therein an imprint on the silicone surface 43. The textured medium 39 can be provided over the entire surface or over a portion of the surface, as desired. The textured medium 39 is then removed from the silicone coating 38 and the prosthesis is cured at elevated temperatures or at room temperature, as desired. The prosthesis manufactured in this manner may then patched with a textured patch as described above.

In another embodiment of the present invention, a layer of unvulcanized silicone with a thickness of less than 0.050 inches is placed around the entire prosthesis which is resting on a mandrel. Two porous or textured-surface sheetings with a thickness of less than 0.050 of an inch are applied to the top and bottom of the unvulcanized silicone layer. The whole assembly is then heated to an elevated temperature of 400° F for 4 hours to cure the silicone. The textured surface surgical prosthesis can then be removed from the mandrel either before or after the heating step, patched and cured for an additional 4 hours at 400° F.

In yet another embodiment of the present invention, a textured surface prosthesis can be transfer, compression or injection molded. As shown in FIG. 8, an injection mold 51 can be provided in the shape of the prosthesis which mold, has a textured surface along the portion of the mold which forms the exterior surface of the prosthesis. Thus, either the upper surface 54 or the lower surface 56 defining the mandrel 58 may be texturized. Silicone material or other suitable biologically compatible material is injected into the mold and prosthesis is formed thereby.

In yet another embodiment of the present invention a textured mandrel as shown in FIG. 6 can be provided having the desired surface topography. The textured mandrel 70 can be dipped or otherwise coated with a silicone material 72. After hardening, the silicone shell may be stripped from the mandrel and the shell turned inside out to provide an exterior surface having the desired texture. As provided above, this textured prosthesis is then patched and filled.

After the prosthesis is manufactured having the desired textured surface it may then be filled with a fluid such as saline, gel or other resilient material as is known in the art. As discussed above, the textured surface may cover the entire exterior wall of the prosthetic body or may only partially cover the exterior surface to provide the desired characteristics. Of course, the roughness and specific surface topography of the prosthesis can be altered by the use of different textured or porous media having corresponding roughness or topography. The textured surface material and the prosthetic material may either or both be made of silicone rubber or other suitable plastic materials.

The materials which may be used to form the shell include silicone rubber, segmental polyurethane, copolymers of silicone, laminates of various forms of silicone, silicone copolymers and polyurethane, and various other elastomers alone or in combination such as those described in U.S. Pat. Nos. 4,592,755 and 4,205,401. In addition, many of the foregoing materials, may be used to form the textured surface on the shell and patch.

The shell to be texturized can be any of a number of styles, sizes and shapes. It may be either single or multi-lumen. It may be of the expandable type such as those used as tissue expanders. It may be circular, oval, crescent-shaped, rectangular, cylindrical such as for penile implants, or a customized shape such as implants for maxillofacial implants.

FIG. 9 shows the texturized surface of an invented prosthesis in a picture taken through a microscope with a 64X magnification. FIG. 10 shows a microscopic 50X magnification of a cross-section of a texturized shell. The three layers 100, 102 and 104 all comprise three layers of the particular shell, and layers 106 and 108 are actually a single layer of textured silicone coated over the shell. The black layer 108 is actually a photographic artifact of the surface as a result of a diffusion of the light at the surface. FIG. 11 is a 50× magnification of a reticulated foam which may be used as a textured medium.

In yet another embodiment of the present invention, a portion of the surface of the prosthesis is provided with a textured surface, such as the patch. This embodiment of the present invention provides a reasonable amount of available textured surface to allow the body to anchor the prosthesis in place.

A unitary textured surface prosthesis having the desired roughness and topography has been disclosed. It will be obvious to one of ordinary skill in the art that a number of modifications can be made to the present invention without departing from the spirit and scope thereof. Therefore, the present invention is defined by the claims and all equivalents thereto and not by the detailed description of the preferred embodiments as provided herein.

We claim:
1. A surgical prosthesis comprising:
   an outer membrane forming an enclosure and comprising a textured exterior surface disposed over at least a portion of said outer membrane, said texture exterior surface being substantially non-absorbent to body fluids and substantially free of fiber and being formed of a plurality of raised portions and indentations, wherein said raised portions are 0.0003 to 0.030 inches in height and 0.0003 to 0.10 in width; and a filler material disposed within said enclosure.

2. The surgical prosthesis of claim 1 wherein said textured exterior surface is disposed over a substantial portion of said outer membrane.

3. The surgical prosthesis of claim 2 wherein said textured exterior surface is disposed over the entire outer membrane.

4. The surgical prosthesis of claim 1 wherein said outer membrane comprises:

a shell comprising a major portion of said outer membrane, and a patch comprising a minor portion of said outer membrane wherein in combination said shell and said patch form a fluid impervious enclosure.

5. The surgical prosthesis of claim 4 wherein both the shell and the patch are texturized.

6. The surgical prosthesis of claim 1 wherein said texturized exterior surface comprises silicone rubber.

7. The surgical prosthesis of claim 1 wherein said surgical prosthesis is a mammary implant.

8. The surgical prosthesis of claim 1 wherein said textured exterior surface comprises irregularly shaped and sized raised portions and indentations.

9. The surgical prosthesis of claim 1 wherein said textured exterior surface comprises regularly shaped and sized raised portions and indentations.

10. A mammary implant comprising:

an outer membrane forming an enclosure and comprising a textured exterior surface formed of flexible, biocompatible, fluid impervious material, said textured surface being substantially non-absorbent to body fluids and substantially free of fiber and being formed of a plurality of raised portions and indentations, wherein said raised portions are 0.0003 to 0.030 inches in height and 0.0003 to 0.10 inches in width; and a filler material disposed within said enclosure and selected from saline gel and combinations thereof.

11. A surgical prosthesis of claim 10 wherein said textural exterior surface is formed of material selected from silicone rubber, segmented polyurethane, copolymers of silicone rubber, laminates of silicone rubber and silicone rubber and polyurethane copolymers and combinations thereof.

12. A surgical prosthesis comprising:

an outer membrane forming an enclosure and formed of a biocompatible elastomeric material comprising a textured exterior surface disposed over at least a portion of said outer membrane, said textured exterior surface comprising a plurality of raised portions substantially free of pores, interstices and fibers, and said textured exterior surface being substantially non-absorbent to body fluids and wherein said raised portions are 0.0003 to 0.030 inches in height and 0.0003 to 0.10 inches in width; and a filler material disposed within said enclosure.

13. The surgical prosthesis of claim 12 wherein said raised portions are alligned substantially transverse to the textured exterior surface.

14. The surgical prosthesis of claim 17 wherein said textured exterior surface is substantially free of pores and interstices which are aligned parallel to a plane defined by said exterior surface.

15. A surgical prosthesis of claim 12 wherein said textural exterior surface is formed of material selected from silicone rubber, segmented polyurethane, copolymers of silcone rubber, laminates of silicone rubber, and silicone rubber and polyurethane copolymers, and combinations thereof.

16. A surgical prosthesis consisting essentially of:

an outer membrane forming an enclosure and formed entirely of elastomeric material and having disposed on at least a portion of the exterior surface thereof a plurality of raised portions and indentations said exterior surface being substantially free of fiber and wherein said raised portions are 0.0003 to 0.030 inches in height and 0.0003 to 0.10 inches in width; and a filler material disposed within said enclosure.

17. A surgical prosthesis of claim 16 wherein said elastomeric material is selected from silicone rubber, segmented polyurethane, copolymers of silicone rubber, laminates of silicone rubber, and silicone rubber and polyurethane copolymers, and combinations thereof.

18. A surgical prosthesis comprising:

an outer membrane comprising a textured exterior surface disposed over at least a portion of said outer membrane, said outer membrane consisting essentially of elastomeric materials selected from silicone rubber, segmented polyurethane, copolymers of silicone rubber, laminates of silicone rubber, and silicone rubber and polyurethane copolymers, and combinations thereof, and said textured surface being substantially free of pores or interstices such that said textured exterior surface substantially nonabsorbent to body fluids and being formed of a plurality of raised portions and indentations, wherein said raised portions are 0.0003 to 0.030 inches in height and 0.0003 to 0.10 inches in width;

an inner membrane formed of elastomeric material substantially impervious to body fluids, wherein said outer and inner membranes in combination form an enclosure; and a filler material disposed within said enclosure.

19. The surgical prosthesis of claim 18 wherein said textured exterior surface is disposed over a substantial portion of said outer membrane.

20. The surgical prosthesis of claim 18 wherein said outer and inner membranes in combination comprises a shell comprising a major portion of said outer membrane, and a patch comprising a minor portion of said outer membrane wherein in combination said shell and said patch form a fluid impervious enclosure.

21. The surgical prosthesis of claim 20 wherein both the shell and the patch are texturized.

22. The surgical prosthesis of claim 18 wherein said texturized exterior surface is comprised of silicone rubber.

23. The surgical prosthesis of claim 18 wherein said outer membrane is substantially free of fibers.

24. The surgical prosthesis of claim 18 wherein said surgical prosthesis is a mammary implant.

* * * * *

UNITED STATES PATENT AND TRADEMARK OFFICE
CERTIFICATE OF CORRECTION

PATENT NO. : 4,960,425

DATED : October 2, 1990

INVENTOR(S) : Yan et al.

It is certified that error appears in the above-identified patent and that said Letters Patent is hereby corrected as shown below:

To the Drawings, add Fig. 9, Fig. 10 and Fig. 11 as shown on the attached page.

Signed and Sealed this

Seventh Day of April, 1992

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,960,425

DATED : October 2, 1990

INVENTOR(S) : Yan et al.

It is certified that error appears in the above-identified patent and that said Letters Patent is hereby corrected as shown below:

Fig. 9

Fig. 10

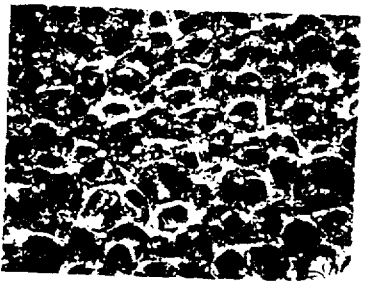

Fig. 11